United States Patent [19]

Dabrah et al.

[11] Patent Number: 5,643,871
[45] Date of Patent: Jul. 1, 1997

[54] ANTITUMOR ANTIBIOTICS

[75] Inventors: Thomas T. Dabrah, Waterford; James A. Matson, Cheshire; Kin Sing Lam, North Haven; Donald R. Gustavson, Torrington; Grace A. Hesler, Branford; Ronald L. Berry, North Branford, all of Conn.

[73] Assignee: Bristol-Meyers Squibb Company, Princeton, N.J.

[21] Appl. No.: 156,479

[22] Filed: Nov. 23, 1993

[51] Int. Cl.$^6$ .................. A61K 38/15; C07K 11/02
[52] U.S. Cl. .................. 514/11; 514/9; 514/2; 530/317
[58] Field of Search .............. 514/11, 9, 2; 530/317; 435/71.3

[56] References Cited

U.S. PATENT DOCUMENTS

| | | | |
|---|---|---|---|
| 4,360,458 | 11/1982 | Koshiyama et al. | 260/112.5 |
| 4,451,456 | 5/1984 | Koshiyama et al. | 424/177 |
| 4,582,639 | 4/1986 | Matson et al. | 260/112.5 |

FOREIGN PATENT DOCUMENTS 2134119A  1/1984  United Kingdom .

OTHER PUBLICATIONS

Yoshida, et al., *The Journal of Antibiotics*, vol. XXI, No. 7, pp. 465–467 (1968).
K. Fox, et al., *Biochem. J.*, vol. 191, pp. 727–742 (1980).
Lim, et al., *Abstract Gen. Meeting Am. Soc. Microbiol.*, 94, 357 (May 23, 1994–May 27, 1994).
A. Dell et al, "Structure Revision of the Antibiotic Echinomycin," *Journal of the American Chemical Society*, 97:9, Apr. a30, 1975, pp. 2497–2502.
*The Merck Manual of Diagnosis & Therapy*, 11th ed. pp. 1368–1370, [1966].
Huang et al, *Anti–Cancer Drug Des.* vol. 1(2), pp. 87–94 (1986); equivalent to CA. 105(5), 35158W.
Olsen et al, *J. Org. Chem.* vol. 51(160, pp. 3079–3085, (1986); equivalent to AN. 86; 414809 (Biosis).

Gauvreau et al, *Cancer: J. Microbiol.*; vol. 30(4), pp. 439–450, (1984); Abstract No. 84:330214 (Biosis).
Konishi et al, *J. Antibiotic*, vol. 34(2), pp. 148–159, 1981, AN. 81:268728 (Biosis).

*Primary Examiner*—Ponnathapura Achutamurthy
*Assistant Examiner*—T. D. Wessendorf
*Attorney, Agent, or Firm*—Sandra M. Nolan

[57] ABSTRACT

The present invention relates to novel antitumor depsipeptides produced by Micromonospora strain 39500, ATCC 55011, and having the structural formula wherein $R_1$ is 2-methylpropanoyl, and $R_2$ is 2-methylppropanoyl, propanoyl or acetyl; or $R_1$ is 3-methylbutanoyl, and $R_2$ is 2-methylpropanoyl or 3-methylbutanoyl; or $R_1$ is propanoyl, and $R_2$ is acetyl or propanoyl.

22 Claims, No Drawings

:::

ANTITUMOR ANTIBIOTICS

BACKGROUND OF THE INVENTION

1. Field of the Invention

The present invention relates to novel antitumor antibiotics, process for their fermentative production, and the producing microorganism per se.

2. Background Art

U.S. Pat. No. 4,360,458 issued to Koshiyama et al on Nov. 23, 1982 discloses an antitumor complex designated BBM-928 (now called luzopeptin) produced by *Actinomadura luzonensis* ATCC 31491. U.S. Pat. No. 4,451,456 issued to Koshiyama et al on May 29, 1984 and UK Published Application No. 2,134,119, published Aug. 4, 1984 disclose the structures of antibiotics BBM-928A, B, C, D and E2 as follows:

Microbially derived quinoxaline antibiotics may be exemplified by echinomycin whose structure is reported in Dell et al, "Structure Revision of the Antibiotic Echinomycin," *Journal of the American Chemical Society*, 1975, 97:2497–2502 as the following:

| Component | $R_1$ | $R_2$ |
|---|---|---|
| A | acetoxy | acetoxy |
| B | acetoxy | hydroxy |
| C | hydroxy | hydroxy |
| D | acetoxy | propionyloxy |
| E2 | hydrogen | hydrogen |

U.S. Pat. No. 4,582,639 issued to Matson et al on Apr. 15, 1986 discloses the antibiotic sandramycin produced by *Nocardioides* sp. strain C49,009, and having the structural formula

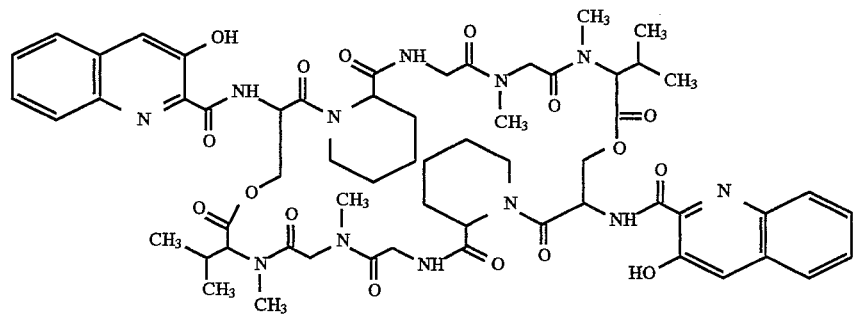

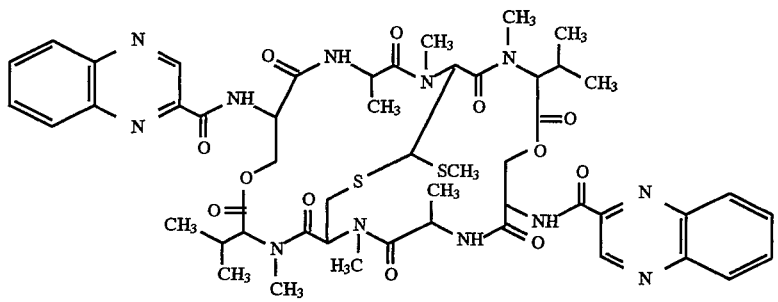

Compounds of the present invention are distinguished over the afore-mentioned depsipeptide antibiotics by the presence of a quinoxaline nucleus and a tetrahydropyridazine moiety.

SUMMARY OF THE INVENTION

The present invention provides novel antitumor antibiotics of the formula (I)

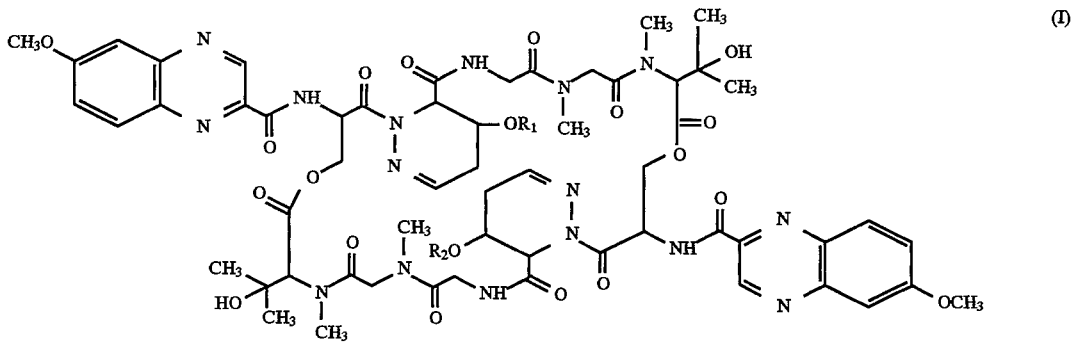

(I)

wherein $R_1$ is 2-methylpropanoyl, and $R_2$ is 2-methylpropanoyl, propanoyl or acetyl; or $R_1$ is 3-methylbutanoyl, and $R_2$ is 2-methylpropanoyl or 3-methylbutanoyl; or $R_1$ is propanoyl, and $R_2$ is acetyl or propanoyl.

Another aspect of the invention provides a pharmaceutical composition which comprises a compound of formula (I) and a pharmaceutically acceptable carrier.

Another aspect of the present invention provides a process for the preparation of the antibiotics of formula (I) which comprises cultivating Micromonospora strain C39500, or an antibiotic producing mutant thereof, in an aqueous nutrient medium containing assimilable sources of carbon and nitrogen under submerged aerobic conditions, and isolating said antibiotics.

Yet another aspect of the present invention provides a method for inhibiting a tumor sensitive to a compound of formula (I) in a mammalian host which comprises administering to said host an antitumor effective amount of a compound of formula (I).

Another aspect of the present invention provides a biologically pure culture of Micromonospora strain C39500 ATCC 55011.

DETAILED DESCRIPTION OF THE INVENTION

The Antibiotics

The antibiotics of the present invention are components of an active complex produced by Micromonospora strain C39500. The antibiotics are cyclic depsipeptides containing a 6-methoxyquinoxaline nucleus as the chromophore and a 4-substituted tetrahydropyridazine moiety. From chemical and spectral information the following structural formulae (I) have been assigned to the antibiotics of the present invention.

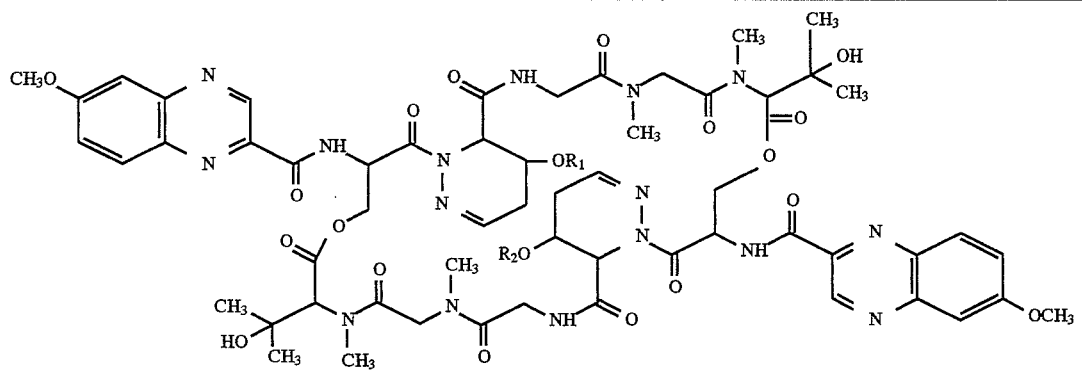

| Compound | R₁ | R₂ |
|---|---|---|
| BMY-45012 | 2-methylpropanoyl ($-COCH(CH_3)_2$) | 2-methylpropanoyl |
| BMY-46404 | 3-methylbutanoyl ($-COCH_2CH(CH_3)_2$) | 2-methylpropanoyl |
| BMY-46405 | 3-methylbutanoyl | 3-methylbutanoyl |
| BMY-46407 | propanoyl ($-COCH_2CH_3$) | acetyl ($-COCH_3$) |
| BMY-46408 | 2-methylpropanoyl | propanoyl |
| BMY-46572 | 2-methylpropanoyl | acetyl |
| BMS-181060 | propanoyl | propanoyl |

Physico-chemical properties of each of the isolated components are described below. Ultraviolet spectra were determined in methanol under neutral, acidic and basic conditions with a Hewlett Packard 8452A diode array spectrophotometer; infrared spectra were determined in KBr pellet with a Perkin Elmer FTIR 1800 spectrophotometer; proton and C13 nuclear magnetic resonance spectra were determined with a Bruker Model AM-500 or Model AM-300 spectrometer using deuterated chloroform as solvent.

BMY-45012

BMY-45012 is the major component of the antibiotic complex. It is a colorless crystalline solid having a molecular formula of $C_{66}H_{84}N_{16}O_{22}$.

Ultraviolet spectrum $\lambda$max nm ($E_{1cm}^{1}\%$):

Neutral MeOH: 210 (567), 258 (502), 350 (131)

Acidic MeOH: 212 (518), 258 (488), 352 (128)

Basic MeOH: 208 (717), 258 (488), 350 (128)

Infra-red spectrum (KBr):3404, 3328, 2976, 2940, 1736, 1674, 1642, 1620, 1418, 1490, 1460, 1418, 1358, 1334, 1290, 1220, 1156, 1110, 1022, 986, 968, 948, 900, 836, 762, 616, 580, cm⁻¹

¹H-NMR spectrum (CDCl₃, 500 MHz): δ(ppm) 9.543 (s, 1H); 8.91 (d, 1H, J=6.25 Hz); 8.86 (d, 1H, J=5.67 Hz); 7.76 (d, 1H, J=7.65 Hz); 7.41 (d, 1H, J=7.65 Hz); 7.39 (s, 1H); 6.95 (d, 1H, J=3.44 Hz); 5.81 (m, 1H); 5.72 (br s, 1H); 5.62 (d, 1H, J=16.7 Hz); 5.52 (d, 1H, j=10.2 Hz); 5.44 (s, 1H); 5.13 (s, 1H) 4.43 (dd, 1H, J=18.1 Hz, 6.3 Hz); 4.29 (d, 1H, J=10.3 Hz); 3.98 (d, 1H, J=18.4 Hz); 3.96 (s, 3H); 3.49 (d, 1H, J=16.7 Hz); 3.27 (s, 3H); 2.91 (s, 3H); 2.62 (d, 1H, J=3.97 Hz); 2.58 (m, 1H); 2.22 (m, 1H); 1.26 (s, 3H); (d, 3H, J=6.81 Hz); 1.03 (d, 3H, J=7.17 Hz); 1.01 (s, 3H).

¹³C-NMR spectrum (CDCl₃, 125 MHz): δ175.58 (ppm) (s); 170.55 (s); 169.14 (s); 168.95 (s); 167.91 (s); 167.49 (s); 163.02 (s); 162.15 (s); 145.81 (s); 143.81 (s); 140.94 (s); 140.90 (d); 136.38 (s); 130.29 (d); 124.58 (d); 106.95 (d); 72.09 (s); 63.45 (t); 61.42 (d); 60.68 (d); 57.12 (d); 55.96 (q); 52.11 (d); 48.75 (t); 41.98 (t); 34.77 (q); 33.41 (q); 32.61 (q); 28.81 (q); 25.96 (t); 25.47 (q); 18.65 (q); 18.35 (q).

BMY-46407

BMY-46407 is a colorless solid with a molecular formula of $C_{63}H_{78}N_{16}O_{22}$.

Ultraviolet spectrum $\lambda$max nm ($E_{1cm}^{1}\%$):

Neutral MeOH: 204 (473), 258 (369), 352 (100)

Acidic MeOH: 204 (451), 258 (358), 352 (92)

Basic MeOH: 204 (904), 258 (356), 352 (91)

Infra-red spectrum (KBr): 3398, 3326, 2958, 1742, 1674, 1644, 1620, 1516, 1490, 1456, 1430, 1414, 1358, 1292, 1222, 1164, 1110, 1024, 986, 968, 948, 898, 862, 836, 812, 768, 618, 580 cm⁻¹

¹H-NMR spectrum (CDCl₃, 500 MHz): δ(ppm) 9.57 (s, 1H); 8.95 (d+d, 1H); 8.87 (d+d, 1H); 7.78 (d, 1H, J=9.75 Hz); 7.43 (s, 1H); 7.42 (d, 1H, J=7.70 Hz); 6.95 (m, 1H); 5.80 (m, 1H); 5.75 (m, 1H); 5.60 (d, 1H, J=16.7 Hz); 5.49 (m, 1H); 5.44 (s, 1H); 5.16 (s, 1H); 4.46 (m, 1H); 4.38 (m, 1H), 3.99 (s, 3H); 3.98 (d, 1H, J=15.3 Hz); 3.51 (d, d, 1H, J=16.7 Hz, 5.8 Hz); 3.26 (s, 3H), 3.25 (s, 3H); 2.93 (s, 3H); 2.92 (s, 3H), 2.65 (m, 1H); 2.46 (m, 1H); 2.25 (m, 1H); 2.03 (s, 3H), 1.29 (s, 3H); 1.03 (d, 3H, J=14.6 Hz).

¹³C-NMR spectrum (CDCl₃, 125 MHz): δ(ppm) 173.17 (s); 170.54 (s); 169.78 (s); 169.14 (s); 167.90 (s); 167.70 (s); 167.56 (s); 163.02 (s); 162.26 (s); 145.72 (s); 143.73 (d); 141.05 (s); 136.53 (s); 130.40 (d); 124.67 (d); 106.59 (d); 72.13 (s); 63.72 (t); 61.00 (d); 60.77 (d); 57.05 (d); 56.02 (q); 52.31 (d); 48.80 (t); 42.01 (t); 34.83 (q); 32.59 (q); 28.86 (q); 27.05 (t); 26.15 (t); 25.50 (q); 20.82 (q); 8.85 (q).

BMY-46572

BMY-46572 is a colorless solid with a molecular formula of $C_{64}H_{80}N_{16}O_{22}$.

Ultraviolet spectrum $\lambda$max nm ($E_{1cm}^{1}\%$):

Neutral MeOH: 208 (622), 258 (506), 350 (128)

Acidic MeOH: 210 (539), 258 (466), 352 (123)

Basic MeOH: 206 (1664), 248 (2478), 352 (124)

Infra-red spectrum (KBr): 3396, 3326, 2976, 2940, 1742, 1674, 1644, 1620, 1516, 1490, 1458, 1418, 1358, 1332, 1290, 1220, 1156, 1110, 1022, 986, 968, 948, 898, 836, 760, 616, 580 cm⁻¹

¹H-NMR spectrum (CDCl₃, 300 MHz): δ(ppm) 9.57 (s, 1H); 8.95 (d+d, 1H); 8.88 (d+d, 1H); 7.78 (d, 1H, J=8.30 Hz); 7.44 (s, 1H); 7.42 (d, 1H, J=7.24 Hz); 6.95 (br s, 1H); 5.81 (m, 1H); 5.74 (m, 1H), 5.65 (d, d, 1H, J=17.0 Hz, 6.4 Hz); 5.52 (m, 1H); 5.46 (s, 1H); 5.16 (s, 1H); 4.47 (m, 1H); 4.37 (m, 1H); 4.00 (d, 1H, J=11.9 Hz); 3.98 (s, 3H); 3.52 (d, d, 1H, J=16.8 Hz, 3.4 Hz); 3.28 (s, 3H); 3.26 (s, 3H); 2.94 (s, 3H); 2.93 (s, 3H); 2.58 (m, 1H); 2.17 (m, 1H); 2.03 (s, 3H); 1.28 (s, 3H); 1.09 (s, 3H); 1.06 (d, 3H, J=2 Hz); 1.03 (d, 3H, J=2.3 Hz ).

$^{13}$C-NMR spectrum (CDCl3, 75 MHz): δ(ppm) 175.68 (s); 170.61 (s); 170.54 (s); 169.78 (s), 169.19 (s); 169.11 (s); 169.00 (s); 168.04 (s); 167.66 (s); 167.59 (s); 163.04 (s); 162.24 (s); 145.75 (s); 143.76 (d); 141.17 (d); 140.96 (s); 136.51 (s); 130.38 (d); 124.68 (d); 106.61 (d); 72.13 (s); 63.71 (t); 63.51 (t); 61.36 (d); 61.01 (d); 60.73 (d); 57.08 (d); 56.02 (q); 52.31 (d); 52.19 (d); 48.85 (t); 42.04 (t); 34.83 (q); 33.43 (d); 32.61 (q); 28.86 (q); 26.13 (t); 25.48(q); 20.85 (q); 18.76 (q); 18.39 (q).

BMS-181060

BMS-181060 is a colorless solid with a molecular formula of $C_{64}H_{80}N_{16}O_{22}$.

Ultraviolet spectrum λmax nm ($E_{1cm}^{1}$%):

Neutral MeOH: 206 (530), 258 (380), 350 (101)

Acidic MeOH: 206 (547), 258 (383), 352 (104)

Basic MeOH: 206 (724), 258 (383), 352 (104)

Infra-red spectrum (KBr): 3398, 3324, 2958, 1740, 1674, 1642, 1620, 1516, 1490, 1458, 1418, 1358, 1292, 1222, 1168, 1110, 1024, 986, 968, 948, 898, 862, 836, 814, 768, 618, 580 cm$^{-1}$ $^{1}$H-NMR spectrum (CDCl$_{3}$, 300 MHz): δ(ppm) 9.86 (s, 1H); 8.96 (d, 1H, J=6.22 Hz); 8.87 (d, 1H, J=5.10 Hz); 7.78 (d, 1H, J=9.97 Hz); 7.44 (s, 1H); 7.41 (d, 1H, J=2.71 Hz); 6.96 (m, 1H): 5.80 (m, 1H); 5.60 (d, 1H, J=16.8 Hz); 5.51 (d, 1H, J=10.1 Hz); 5.46 (s, 1H); 5.15 (s, 1H); 4.46 (d, d, 1H, J=17.9 Hz, 6.02 Hz): 4.37 (d, d, 1H, J=11.3 Hz, 2.60 Hz); 3.99 (d, 1H, J=17.2 Hz); 3.98 (s, 3H); 3.51 (d, 1H, J=16.7 Hz); 3.26 (s, 3H); 2.92 (s, 3H); 2.64 (d, d, 1H J=18.6 Hz, 3.65 Hz); 2.46 (m, 1H); 2.24 (d, q, 1H, J=7.38 Hz); 2.17 (m, 1H); 1.28 (s, 3H); 1.03 (s, 3H); 1.02 (t, 3H, J=7.24 Hz).

$^{13}$C-NMR spectrum (CDCl$_{3}$, 75 MHz): δ (ppm) 173.16 (s); 170.56 (s); 169.13 (s); 169.04 (s); 167.82 (s); 167.56 (s); 163.02 (s); 162.27 (s); 145.62 (s); 143.70 (d); 141.09 (d); 136.54 (s); 130.40 (d); 124.69 (d); 106.57 (d); 72.13 (s); 63.66 (t); 60.99 (d); 60.73 (d); 57.10 (d); 56.03 (q); 52.30 (d); 48.81 (t); 42.04 (t); 34.79 (q); 32.60 (q); 28.86 (q); 27.06 (t); 26.13 (t); 25.49 (q); 8.86 (q).

BMY-46408

BMY-46408 is a colorless solid with a molecular formula of $C_{65}H_{82}N_{16}O_{22}$.

Ultraviolet spectrum λmax nm ($E_{1cm}^{1}$%):

Neutral MeOH: 208 (500), 258 (460), 352 (120)

Acidic MeOH: 210 (430), 258 (412), 352 (100)

Basic MeOH: 206 (968), 250 (1788), 352 (103)

Infra-red spectrum (KBr): 3398, 3330, 2976, 2940, 1740, 1674, 1644, 1620, 1516, 1490, 1460, 1418, 1356, 1290, 1220, 1166, 1110, 1024, 986, 968, 948, 898, 836, 758, 666, 580 cm$^{-1}$ $^{1}$H-NMR spectrum (CDCl$_{3}$, 300 MHz): δ(ppm) 9.55 (s, 1H); 8.95 (t, 1H, J=6.5 Hz); 8.87 (d, 1H, J=5.52 Hz); 7.76 (d, 1H, J=9.96 Hz); 7.42 (s, 1H); 7.41 (d, 1H, J=8.25 Hz); 6.95 (m, 1Hz); 5.79 (m, 1H); 5.60 (d, d, 1H, J=16.8 Hz, 6.9 Hz); 5.49 (d, 1H, J=10.7 Hz); 5.43 (s, 1H); 5.15 (s, 1H); 4.46 (m, 1H); 4.37 (m, 1H); 3.99 (d, 1H, J=13.3 Hz); 3.97 (s, 3H); 3.50 (d, 1H, J=16.7 Hz); 3.27 (s, 3H); 3.25 (s, 3H); 2.92 (s, 3H); 2.65 (m, 1H); 2.58 (m, 1H); 2.45 (m, 1H); 2.25 (m, 1H); 1.28 (s, 3H); 1.06 (d, 3H, J=6.9 Hz); 1.04 (t, 3H, J=4.8 Hz); 1.02 (d, 3H, J=7.14 Hz).

$^{13}$C-NMR spectrum (CDCl$_{3}$, 75 MHz): δ(ppm) 175.65 (s); 173.13 (s); 170.58 (s); 170.53 (s); 169.16 (s); 169.04 (s); 168.98 (s); 167.77 (s); 167.53 (s); 163.02 (s); 162.22 (s); 145.75 (s); 143.75 (d); 141.10 (d); 140.97 (s); 136.46 (s); 130.35 (d); 124.63 (d); 106.61 (d); 72.11 (s); 63.64 (t); 63.50 (t); 61.40 (d); 61.01 (d); 60.73 (d); 57.12 (d); 55.99 (q); 52.26 (d); 52.15 (d); 48.79 (t); 42.07 (t); 41.96 (t); 34.79 (q); 33.42 (d); 32.62 (q); 32.59 (q); 28.83 (q); 27.05 (t); 26.06 (t); 25.49 (q); 18.71 (q); 18.37 (q); 8.80 (q).

BMY-46404

BMY-46404 is a colorless solid with a molecular formula of $C_{67}H_{86}N_{16}O_{22}$.

Ultraviolet spectrum λmax nm ($E_{1cm}^{1}$%):

Neutral MeOH: 210 (450), 258 (423), 350 (101)

Acidic MeOH: 212 (390), 258 (433), 352 (104)

Basic MeOH: 206 (1061), 250 (1178), 352 (120)

Infra-red spectrum (KBr): 3404, 3330, 2966, 1738, 1674, 1646, 1620, 1514, 1490, 1460, 1418, 1358, 1334, 1292, 1250, 1220, 1158, 1110, 1024, 986, 968, 948, 898, 836, 760, 614, 580 cm$^{-1}$ $^{1}$H-NMR spectrum (CDCl$_{3}$, 300 MHz): δ(ppm) 9.63 (s, 1H); 8.96 (d, 1H, J=6.3 Hz); 8.91 (d, 1H, J=6.3 Hz); 8.86 (d, d, 1H, J=11.3 Hz, 6.1 Hz); 7.78 (d, d, 1H, J=5.20 Hz, 1.45 Hz); 7.43 (s, 1H); 7.41 (d, 1H, J=8.2 Hz); 6.96 (m, 1H); 5.81 (m, 1H); 5.74 (d, 1H, J=9.4 Hz); 5.57 (d, d, 1H J=12.9 Hz, 4.85 Hz); 5.50 (t, 1H, J=11.2 Hz); 5.40 (s, 1H); 5.16 (s, 1H); 5.14 (s, 1H); 4.46 (m, 1H); 4.36 (d, d, 1H, J=11.4 Hz, 2.8 Hz); 4.31 (d, d, 1H, J=11.4 Hz, 2.5 Hz); 3.97 (d, d, 1H, J=17 Hz, 6.15 Hz); 3.97 (s, 3H); 3.51 (d, 1H, J=16.5 Hz); 2.92 (s, 3H); 2.91 (s, 3H); 2.62 (m, 1H); 2.58 (m, 1H); 2.24 (m, 1H), 2.21 (m, 1H); 1.95 (m, 1H); 1.07 (d, 3H, J=6.9 Hz); 1.05 (d, 3H, J=7.05 Hz); 0.88 (d, 6H, J=7.4 Hz) .

$^{13}$C-NM$_{R}$ spectrum (CDCl$_{3}$, 75 MHz): δ(ppm) 175.60 (s); 171.76 (s); 170.59 (s); 170.54 (s); 169.17 (s); 169.10 (s); 169.01 (s); 167.94 (s); 167.76 (s); 167.52 (s); 167.34 (s); 163.02 (s); 162.22 (s); 145.77 (s); 143.78 (d); 140.98 (s); 136.48 (s); 130.34 (d); 124.63 (d); 106.64 (d); 72.16 (s); 72.12 (s); 63.72 (t); 63.48 (t); 61.48 (d); 61.07 (d); 60.88 (d); 60.72 (d); 57.20 (d); 57.09 (d); 56.00 (q); 52.26 (d); 52.16 (d); 48.96 (t); 48.79 (t); 42.45 (t); 41.99 (t); 34.80 (q); 33.45 (d); 32.64 (q); 32.58 (q); 29.66 (t); 29.42 (t); 28.83 (q); 26.18 (t); 25.99 (t); 25.51 (q); 25.24 (q); 22.35 (q); 22.15 (q); 18.68 (q); 18.39 (q).

BMY-46405

BMY-46405 is a colorless solid with a molecular formula of $C_{68}H_{88}N_{16}O_{22}$.

Ultraviolet spectrum λmax nm ($E_{1cm}^{1}$%):

Neutral MeOH: 210 (540), 258 (499), 350 (130)

Acidic MeOH: 210 (540), 258 (493), 350 (132)

Basic MeOH: 208 (606), 258 (490), 350 (128)

Infra-red spectrum (KBr): 3398,.3324, 2974, 1738, 1672, 1642, 1620, 1518, 1490, 1460, 1418, 1358, 1334, 1292, 1250, 1220, 1162, 1110, 1022, 986, 968, 948, 898, 836, 762, 616, 582 cm$^{-1}$ $^{1}$H-NMR spectrum (CDCl$_{3}$, 300 MHz): δ(ppm) 9.57 (s, 1H); 8.95 (d, 1H, J=6.21 Hz); 8.87 (d, 1H, J=5.82 Hz); 7.82 (d, 1H, J=9.24 Hz); 7.55 (d, 1H, J=2.5 Hz); 7.46 (d, d, 1H, J=9.21 Hz, 2.67 Hz); 6.95 (s, 1H); 5.80 (d, 1H, J=6.09 Hz); 5.77 (br s, 1H); 5.57 (d, 1H, J=16.7 Hz) 5.50 (d, 1H, J=11.2 Hz); 5.48 (s, 1H); 5.16 (s, 3H); 4.49 (d, d, 1H, J=18 Hz, 6.33 Hz); 4.37 (d, d, 1H, J=11.3 Hz, 2.6 Hz); 4.00 (s, 3H); 3.99 (d, 1H, J=8.22 Hz); 3.51 (d, 1H, J=16.7 Hz); 3.24 (s, 3H); 2.92 (s, 3H); 2.63 (d, d, 1H, J=18.4 Hz, 4.2 Hz); 2.25 (m, 1H); 2.18 (m, 1H); 1.95 (m, 1H): 1.28 (s, 3H); 1.03 (s, 3H); 0.89 (s, 3H); 0.87 (s, 3H).

$^{13}$C-NMR spectrum (CDCl$_{3}$, 75 MHz): δ(ppm) 171.77 (s); 170.57 (s); 169.15 (s); 167.80 (s); 167.35 (s); 162.99 (s); 162.34 (s); 145.43 (s); 143.66 (s); 141.11 (s); 141.11 (d); 136.65 (s); 130.43 (d); 124.74 (d); 106.54 (d); 72.17 (s); 63.72 (t); 61.07 (d); 60.87 (d); 57.14 (d); 56.06 (q); 52.30

(d); 48.97 (t); 41.97 (t); 34.85 (q); 34.21 (d); 32.59 (q); 29.68 (t); 29.45 (t); 28.85 (q); 26.18 (t); 25.53 (q); 25.26 (q); 22.37 (q); 22.17 (q).

The Producing Organism

Antibiotics of the present invention may be prepared by fermentation of a strain of Micromonospora capable of producing the antibiotics. The preferred producing organism is a novel strain of Micromonospora designated herein as Micromonospora strain C39500. A biologically pure culture of strain C39500 has been deposited with the American Type Culture Collection (ATCC) in Rockville, Md., under the BUDAPEST TREATY ON THE INTERNATIONAL RECOGNITION OF THE DEPOSIT OF MICROORGANISMS FOR THE PURPOSES OF PATENT PROCEDURE, and all restrictions on the availability to the public of the deposited microorganism will be irrevocably removed upon the granting of a patent from this application. The deposited culture has been assigned the accession number ATCC 55011. The characteristics of strain C39500 are set forth below.

(a) Cultural characteristics: The cultural characteristics of strain C39500 were examined on 22 media used for the cultivation and taxonomic description of actinomycetes. Good growth was obtained on yeast extract-malt extract agar (ISP medium No. 2), ISP Medium No. 2 supplemented with 0.15% $CaCO_3$, ATCC Medium No. 5 (sporulation agar), ATCC Medium No. 172 (Nz amine with soluble starch and glucose), and modified Bennett's medium. Growth was fair on Emerson agar and inorganic salts-starch agar (ISP Medium 4); and poor or scant growth was obtained on the following agars: trypticase soy nutrient, oatmeal nitrate, Czapek's (a well known sucrose-nitrate agar), glucose asparagine, maltose tryptone, peptone iron, xanthine, tomato juice, glycerol asparagine (ISP Medium 5), casein starch, Actinomycete isolation, tyrosine, thin potato carrot, and potato dextrose.

(b) Physiological characteristics: The carbon utilization pattern of strain C39500 was determined after a 2 week incubation at 28° C. using Luedemann's agar supplemented with various carbon sources (1%). Strain C39500 was found to utilize glucose, galactose, lactose, trehalose, cellobiose, mannose, rhamnose, and xylose. Utilization of arabinose, salicin, dulcitol, glycerol, melibiose, raffinose, melezitose, inositol, and sorbitol was doubtful. Ribose, sucrose, and mannitol as sole carbon sources did not support any growth.

A temperature gradient incubator was utilized to determine the range at which this strain will grow. The temperature range for growth is about 23° C. to about 43° C., with the optimal range being about 28° C. to about 38° C.

(c) Morphology: The micromorphology of strain C39500 in situ was examined on various media. Open web sporulation, monopodially-borne monospores, monospores borne directly on the filamentous hyphae, and clusters of monospores were all observed.

(d) Cell wall composition: Cellulose thin-layer chromatography was performed on dried cells hydrolyzed with 6N HCl, and strain C39500 was determined to contain the meso isomer of diaminopimelic acid.

The above characteristics of strain C39500 indicate that it is a species of Micromonospora.

Antibiotic Production

The antibiotics of the present invention are prepared by cultivating an antibiotic producing strain of Micromonospora, preferably a strain of Micromonospora having the identifying characteristics of strain C39500 (ATCC 55011), or a mutant or a variant thereof, in a conventional aqueous nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention.

The nutrient medium should contain an appropriate carbon source such as glucose, lactose, galactose, fructose, mannose, rhamnose and soluble starch. An assimilable nitrogen source such as fish meal, Pharmamedia, yeast extract, Bacto-liver, peptone, peanut meal, cottonseed meal or corn-steep liquor should be employed. Nutrient inorganic salts can also be incorporated in the medium so as to provide sodium, potassium, ammonium, calcium, phosphate, sulfate, chloride, bromide, nitrate, carbonate and like ions. Trace elements such as copper, manganese, iron, zinc, etc. are added to the medium if desired, or they may be present as impurities of other constituents of the media. It was also determined that addition of L-valine to the medium enhanced the production of BMY-45012.

Antibiotic production can be effected at any temperature conducive to satisfactory growth of the producing organism, e.g. from about 23° to about 43° C.; preferably from about 28° C. to about 38° C., most preferably at about 28° C. The fermentation may be carried out in flasks or in laboratory or industrial fermentors of various capacity. When tank fermentation is to be used, it is desirable to produce a vegetative inoculum in a nutrient broth by inoculating a small volume of the culture medium with a slant or a lyophilized culture of the producing organism. After obtaining a viable and active inoculum in this manner, it is transferred aseptically to the fermentation tank charged with production medium for large scale production of the present antibiotics. The medium in which the vegetative inoculum is prepared can be used the same as, or different from, that utilized in the tank as long as it is such that a good growth of the producing organism is obtained. Further agitation may be provided by a mechanical impeller. Antifoam agents such as lard oil or silicone oil may be added if needed. Antibiotic production may be monitored by high pressure liquid chromatography or by a conventional biological assay.

Although strain C39500 is preferably used to produce the antibiotics of the present invention, it is understood that the present invention is not limited to use of the particular strain C39500 or to organisms fully answering the above description. It is especially intended to include other antibiotic producing strains or mutants of the said organism which can be produced from the described organism by known means such as X-radiation, ultraviolet radiation, treatment with nitrogen mustards, phage exposure, and the like.

The antibiotics of the present invention may be isolated from the fermentation broth and further purified using conventional methodologies such as solvent extraction, and various chromatogragphic techniques. One preferred isolation/purification sequence illustrative of the present invention is described in Example 5.

Biological Activity

Antibiotics of the present invention were evaluated against transplantable P388 murine leukemia, generally following the protocols of the National Cancer Institute (see Cancer Chemotherapy Report, Part 3, 3, 1–103, 1972). $CDF_1$ female mice were implanted intraperitoneally with a tumor inoculum of $10^6$ ascites cells of P388, and treated with various doses of test compounds. The compounds were administered intraperitoneally once daily for five consecutive days starting on the day after tumor implantation. The ratio of median survival time for a treated group and that for the saline-treated control group was determined and expressed as %T/C. A compound with a %T/C value of greater or equal to 125 is considered to have significant antitumor activity. The result of P388 evaluation of the antibiotics of the present invention is presented in the following Table.

In Vivo Antitumor Activity
Against P388 Leukemia (ip)

| Compound | Dose* (mg/kg/day) | Median Survival Time | % T/C | Body Weight Change on Day 4 |
|---|---|---|---|---|
| BMY-45012 | 0.7 | 9.5 | 95 | −0.1 |
|  | 0.2 | 14.5 | 145 | −0.7 |
|  | 0.05 | 14.5 | 145 | 0.3 |
|  | 0.02 | 11.5 | 115 | −0.4 |
| BMY-46407 | 2.0 | Tox | Tox | — |
|  | 0.7 | Tox | Tox | — |
|  | 0.2 | Tox | Tox | −0.01 |
|  | 0.05 | 13.5 | 135 | −0.0 |
|  | 0.02 | 12.0 | 120 | 1.0 |
| BMY-46572 | 0.03 | 14.0 | 140 | −0.0 |
|  | 0.01 | 12.5 | 125 | 0.5 |
|  | 0.003 | 11.0 | 110 | 0.4 |
| BMS-181060 | 0.81 | Tox | Tox | — |
|  | 0.27 | Tox | Tox | 0.7 |
|  | 0.09 | 10.0 | 91 | −0.9 |
|  | 0.03 | 14.0 | 127 | 0.0 |
|  | 0.01 | 14.0 | 127 | 0.1 |
|  | 0.003 | 11.5 | 105 | 1.0 |
| BMY-46408 | 2.0 | Tox | Tox | — |
|  | 0.7 | 8.5 | 85 | 0.3 |
|  | 0.2 | 15.5 | 155 | 0.2 |
|  | 0.05 | 15.5 | 155 | −0.4 |
|  | 0.02 | 15.0 | 150 | −0.1 |
| BMY-46404 | 2.0 | 8.5 | 80 | −0.7 |
|  | 0.7 | 16.5 | 165 | −0.3 |
|  | 0.2 | 13.5 | 135 | −0.0 |
|  | 0.05 | 14.0 | 140 | 0.2 |
|  | 0.02 | 13.0 | 130 | −0.1 |
| BMY-46405 | 2.0 | Tox | Tox | — |
|  | 0.7 | Tox | Tox | — |
|  | 0.2 | Tox | Tox | −3.4 |
|  | 0.05 | 17.5 | 175 | −0.8 |
|  | 0.02 | 14.0 | 140 | −0.8 |

In an iv/iv P388 leukemia protocol (analogous to the above described protocol except the leukemic cells were implanted, and the test drug was administered, intravenously), BMY-45012 showed a maximum %T/C of 113 at a dose level of 0.010 mg/kg/dose administered according to the above schedule.

BMY-45012 was also evaluated against Madison 109 (M109) lung carcinoma model in mice, generally following the protocols reported in W. Rose, "Evaluation of Madison 109 Lung Carcinoma as a Model for Screening Antitumor Drugs," Cancer Treatment Reports, 65, No. 3–4, p. 299- (1981). Briefly, $CDF_1$ female mice were implanted intraperitoneally (ip) with 0.5 ml or subcutaneously (sc) with 0.1 ml of a 2% brei (w/v) of M109 lung carcinoma. The test compound was administered intraperitoneally (in ip tumor implant groups) or intravenously (in sc tumor implant groups) at various dosage levels to groups of mice on days 2, 6 and 10 after tumor implantation. The median survival time and %T/C values were determined as described above. In the ip/ip model (ip tumor implantation/ip drug administration), BMY-45012 showed a maximum %T/C of 131 at a dose of 0.05 mg/kg/dose; whereas in the sc/iv model (sc tumor implantation/intravenous drug administration), the compound was not significantly active.

As indicated by the mouse tumor data provided above, compounds of the present invention are useful as antitumor agents for inhibition of mammalian malignant tumors such as P-388 leukemia and Madison 109 lung carcinoma.

The invention includes within its scope pharmaceutical compositions containing an effective tumor-inhibiting amount of an antibiotic of formula (I) in combination with an inert pharmaceutically acceptable carrier or diluent. Such compositions may also contain other active antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

For use as antitumor agents, compounds of the present invention may be administered in a manner similar to that employed for other known antitumor agents. The optimal dosages and regimens of a compound of formula (I) for a given mammalian host can be readily ascertained by those skilled in the art. It will, of course, be appreciated that the actual dose used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The present invention is illustrated by the following examples which are not intended to be construed as limiting the scope of the invention.

EXAMPLE 1

Preparation of cryopreservative culture of Micromonospora strain C39500.

Micromonospora strain C39500 was maintained as a cryopreserved culture stored at −80° C. in a Revco ultralow temperature freezer. To prepare a cryopreserved culture, strain C39500 was grown in test tubes on slants of yeast extract-malt extract agar (supplemented with 0.15% calcium carbonate) which consists of:

| Dextrose | 4.0 g |
|---|---|
| Yeast extract | 4.0 g |
| Malt extract | 10.0 g |
| Calcium carbonate | 1.5 g |
| Agar | 15 g |
| Deionized water | q.s. to 1 liter |

The agar slant was incubated at 28° C. for 7–10 days. Vegetative culture was prepared by transferring the surface growth aseptically from the slant culture to a 500 ml Erlenmeyer flask containing 100 ml of a sterile vegetative medium consisting of:

| Lactose | 10 g |
|---|---|
| Soluble starch | 30 g |
| Fish meal | 10 g |

|                   |      |
| ----------------- | ---- |
| Calcium sulfate   | 6 g  |
| Calcium carbonate | 3 g  |
| Deionized water   | q.s. to 1 liter |

The vegetative culture was incubated at 28° C. for 72 hours on a rotary shaker set at 250 rev/min. The vegetative culture was mixed with equal volume of cryoprotective solution consisting of:

|                 |         |
| --------------- | ------- |
| Sucrose         | 100 g   |
| Glycerol        | 200 g   |
| Deionized water | q.s. to 1 liter |

Four ml portions of this mixture were transferred to sterile cryogenic tubes (5 ml capacity, Corning) and were frozen in a dry ice-acetone bath. The frozen vegetative cultures were then stored at −80° C. in a Revco ultralow temperature freezer.

EXAMPLE 2

Preparation of vegetative culture of Micromonospora strain C39500.

Vegetative culture was prepared by transferring 4 ml of the cryopreserved culture to a 500 ml Erlenmeyer flask containing 100 ml of a sterile vegetative medium having the same composition as the cryopreserved vegetative culture. Strain C39500 was incubated at 28° C. for 72 hours on a rotary shaker set at 250 rev/min.

EXAMPLE 3

Fermentation of antibiotics in shake flask culture.

Four ml of the vegetative culture of Example 2 was inoculated into 500 ml Erlenmeyer flasks each containing 100 ml of a production medium. The production culture was incubated at 28° C. on a rotary shaker set at 250 rev./min. Antibiotic production was monitored by HPLC and production at day 6 of fermentation in each medium was determined as follows:

| Antibiotic | Medium A    | Medium B  | Medium C   |
| ---------- | ----------- | --------- | ---------- |
| BMY-45012  | 99.3 µg/ml  | 295 µg/ml | 101 µg/ml  |
| BMY-46404  | 17.4 µg/ml  | 4.2 µg/ml | 29.5 µg/ml |
| BMY-46405  | 0           | 0         | 9.8 µg/ml  |
| BMY-46407  | 6.9 µg/ml   | 0         | 11.9 µg/ml |
| BMY-46408  | 22.3 µg/ml  | 0         | 49.1 µg/ml |
| BMY-46572  | 35.9 µg/ml  | 7.4 µg/ml | 0          |
| BMS-181060 | 0           | 0         | 42.8 µg/ml |

Production medium A: Glucose (10g), soluble starch (30g), Pharmamedia (10g, Traders Protein), debittered brewer's yeast (5g, Nutrex of Universal Foods Corp.), calcium sulfate (6g), calcium carbonate (3g), deionized water (q.s. to 1L)
Production medium B: Medium A supplemented with L-valine (1 g/L)
Production medium C: Glucose (10 g), soluble starch (30g), Bacto-liver (10 g, Difco), calcium sulfate (6 g), calcium carbonate (5 g), deionized water (q.s. to 1 liter)

EXAMPLE 4

Fermentation of BMY-45012 in fermentor culture.

A vegetative culture (100 ml) was prepared as described in Example 2. Twenty ml of the vegetative culture were transferred into a 2L Erlenmeyer flask containing 400 ml of the same vegetative medium. Three vegetative cultures were combined and inoculated aseptically into a Biolafitte fermentor (50 L nominal volume) containing 30 L of production medium B as described in Example 3. The fermentation was carried out at 28° C., aeration of 0.7 volume per minute and the agitation set at 250 rev/min. Antibiotic production at day 6 of fermentation, determined by HPLC analysis, was as follows:

|            |            |
| ---------- | ---------- |
| BMY-45012  | 401 µg/ml  |
| BMY-46404  | 5.9 µg/ml  |
| BMY-46405  | 0          |
| BMY-46407  | 0          |
| BMY-46408  | 0          |
| BMY-46572  | 14.6 µg/ml |
| BMS-181060 | 0          |

EXAMPLE 5

Isolation and purification of antibiotics.
(a) Preparation of Crude Extract A

Raw fermentation broth (30 L) was mixed with an equal volume of ethyl acetate (30 L) in a polypropylene tank and stirred for 1 hour using an air-driven mixer (Fawcett Co., Inc., Ridgefield, Ohio, Model #101A). Four large scoops of Dicalite (diatomaceous earth manufactured by Grefco, Inc., Torrance, Calif.) (approximately 2 kg) were mixed into the suspension. The resulting mixture was filtered using an Ametek 12" Centerslung basket centrifuge (Model #84). The filtrate was allowed to develop into immiscible phases which were subsequently separated. The organic, ethyl acetate layer was concentrated in vacuo in a Buchi R175 EX rotary evaporator to yield 36.6 g of dark brown residue A.

b) Dicalite Chromatography of Residue A

A slurry of residue A (36.6 g), 100 mL of chloroform/methanol (2:1) solvent mixture, and Dicalite (100 g) was prepared in a 500 mL round bottom flask. After thorough mixing, the slurry was evaporated to dryness in vacuo in rotary evaporator. The resulting residue was added to a sintered glass Buchner funnel (7 cm [i.d.]×10 cm height) prepacked with 25 g of Dicalite. Elution under gentle pressure was done with the following eluotropic series; hexanes (1L), 20% acetone/hexane (500mL), toluene (1L), chloroform (1L), ethyl acetate (1L), and methanol (500mL). The chloroform eluant was concentrated to dryness in vacuo in a rotary evaporator to give 9.4 g of residue B.

(c) Vacuum Liquid Chromatography of Residue B

A sintered-glass Buchner filter funnel with a fritted disk (Kontes Scientific Glassware K-954100 Buchner funnel, medium [M]pore size 10–15 microns, 4.5 cm [i.d.]×10 cm ht) was dry packed to a height of 5 cm with 30 g of TLC-grade silica gel (silica gel 60, cat. #7730, E. Merck, Darmstadt, Germany). The adsorbent was allowed to settle by gentle tapping under gravity followed by the application of vacuum to give a uniform and tightly packed hard cake. Vacuum was released and chloroform (100 mL) was added to the surface of the adsorbent. The vacuum was again applied and the column sucked dry.

Residue B (9.4 g) was preadsorbed on a small amount of silica gel and uniformly applied to the top of the column. Elution commenced under gentle vacuum with the following eluotropic series; 500 mL each of hexane/chloroform (1:1), chloroform, 1% methanol in chloroform, 2% methanol in chloroform, 3% methanol in chloroform, 4% methanol in chloroform, 5% methanol in chloroform and 10% methanol in chloroform. Thin-layer chromatography monitoring of the fractions (Merck Silica Gel 60 F-254 plates (2.5 cm ×10 cm ×0.25 cm methanol:chloroform (1:9), UV visualization at 254 nm and 366 nm) showed the 1% methanol in chloroform eluant to be highly enriched in a zone at $R_f$ 0.6, which showed purple and intense blue fluorescenses under ultraviolet short and long wavelength lights, respectively. Concentration in vacuo of the 1% methanol in chloroform eluant, yielded residue C (2.96 g) which was recrystallized from ethyl acetate to give a colorless solid.

(d) Preparative HPLC of Residue C

Examination of a sample of residue C by analytical HPLC revealed it was composed of a major component (42%, BMY-45012) and several minor congeners. Semi-preparative HPLC was therefore used to resolve this complex into its individual components. The semi-preparative HPLC system consisted of the waters 600E Multi-Solvent Delivery System; knauer Model 87 Variable Wavelength Detector, shimadzu CR 501 chromatopac Integrator, waters associates Model U6K injector (with 2 mL sample loop). The columns used were waters RCM 25×10 cm cartridge columns (segmented columns) or Zorbax Rx $C_{18}$ (9.4×250 mm) as conditions dictated. The eluants were either (i) 4 parts water (0.1M ammonium acetate), 4 parts acetonitrile ($CH_3CN$), 1 part methanol (MeOH), 1 part tetrahydrofuran (THF) or (ii) 55 parts water, 25 parts acetonitrile, 20 parts tetrahydrofuran and were pumped at flow rates of 7.0 mL/min or 8 mL/min or 10 mL/min., as the situation demanded for the best resolution of peaks. The HPLC was monitored by absorbance at 320 nm for all the separations.

A waters RCM 25×30 cartridge column (3-segmented columns, µ Bondapak $C_{18}$, 10 µ, 125Å pore size) was equilibrated with the mobile phase consisting of 4 parts 0.1M ammonium acetate, 4 parts acetonitrile, 1 part methanol and 1 part tetrahydrofuran, at a flow rate of 8 mL/min. After the equilibration (5-column volumes), a sample of residue C (250 mg dissolved in 700 µL of THF/DMSO) was injected onto the column. The HPLC separation was monitored with UV at 320 nm and peaks corresponding to 8 components were separately collected. Additional injections of the crude mixture were made and similar peaks were pooled. The eluants were extracted with chloroform and the solvents evaporated under reduced pressure to give colorless solids. BMY-46407 was the first compound to elute from the column followed by BMY-46572, BMS-181060-01, BMY-46408, BMY-45012, BMY-46404 and BMY-46405 in that order.

The isolates were further purified by HPLC using the following procedure and conditions. A sample of the compound was dissolved in dimethylsulfoxide: tetrahydrofuran (1:1) (ca. 1 mg sample/10 µl of solvent) and injected onto the HPLC column which had been equilibrated with the mobile phase. The fractions containing the desired compound were collected, extracted with chloroform, and the solvent evaporated to provide analytically pure samples of the compounds.

| Column | ZORBAX Rx $C_{18}$ (9.4 × 250 mm) | WATERS RCM 25 × 30 cm cartridge columns (segmented columns) |
|---|---|---|
| Mobile Phase | $H_2O:CH_3CN:THF$ (55:25:20) | 0.1M $NH_4OAc:CH_3CN$: MeOH:THF (40:40:10:10) |
| Flow Rate | 4 ml/min. | 7*, 8 or 10‡ ml/min. |
| Compounds Purified | BMY-46572 BMS-181060 | Y-46405*, BMY-46404, Y-46407, BMY-46408, Y-45012‡ |

We claim:
1. A compound having the formula

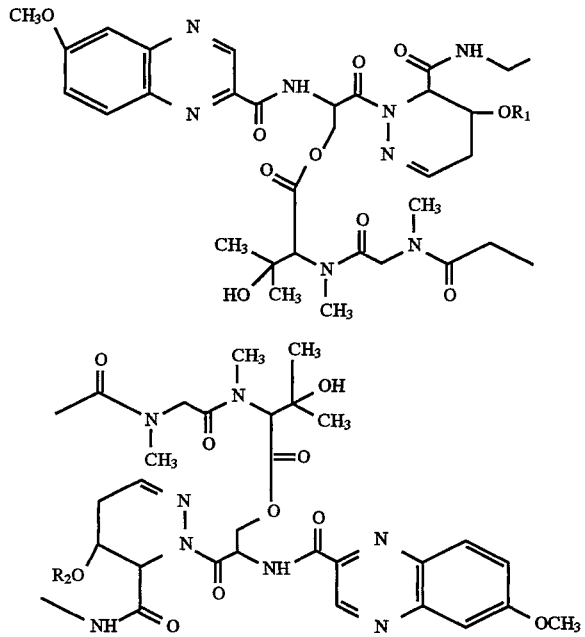

wherein $R_1$ is 2-methylpropanoyl, and $R_2$ is 2-methylpropanoyl, propanoyl or acetyl; or $R_1$ is 3-methylbutanoyl, and $R_2$ is 2-methylpropanoyl or 3-methylbutanoyl; or $R_1$ is propanoyl, and $R_2$ is acetyl or propanoyl.

2. A compound of claim 1 wherein $R_1$ is 2-methylpropanoyl, and $R_2$ is 2-methylpropanoyl.

3. A compound of claim 1 wherein $R_1$ is 2-methylpropanoyl, and $R_2$ is propanoyl.

4. A compound of claim 1 wherein $R_1$ is 2-methylpropanoyl, and $R_2$ is acetyl.

5. A compound of claim 1 wherein $R_1$ is 3-methylbutanoyl, and $R_2$ is 2-methylpropanoyl.

6. A compound of claim 1 wherein $R_1$ is 3-methylbutanoyl, and $R_2$ is 3-methylbutanoyl.

7. A compound of claim 1 wherein $R_1$ is propanoyl, and $R_2$ is acetyl.

8. A compound of claim 1 wherein $R_1$ is propanoyl, and $R_2$ is propanoyl.

9. A method for treating leukemia or lung carcinoma in a mammalian host which comprises administering to said host an antitumor effective amount of the compound of claim 1.

10. A pharmaceutical composition which comprises a compound of claim 1 and a pharmaceutically acceptable carrier.

11. a method of treating M109 lung carcinoma in a mammalian host comprising administering to said host an antitumor effective amount of the compound of claim 2.

12. A pharmaceutical composition for treating M109 lung carcinoma comprising an antitumor effective amount of the compound of claim 2 and a pharmaceutically acceptable carrier.

13. A method of treating leukemia in a mammalian host which comprises administering to said host an antitumor effective amount of the compound of claim 2.

14. A pharmaceutical composition for treating leukemia comprising an antitumor effective amount of the compound of claim 2 and a pharmaceutically acceptable carrier.

15. A method of treating M109 lung carcinoma in a mammalian host which comprises administering to said host an antitumor effective amount of the compound of claim 8.

16. A pharmaceutical composition for treating M109 lung carcinoma comprising an antitumor effective amount of the compound of claim 8 and a pharmaceutically acceptable carrier.

17. A method of treating leukemia in a mammalian host which comprises administering to said host an antitumor effective amount of the compound of claim 8.

18. A pharmaceutical composition for treating leukemia comprising an antitumor effective amount of the compound of claim 8 and a pharmaceutically acceptable carrier.

19. The method of claim 11 wherein the compound is administered interperitoneally.

20. The method of claim 13 wherein the compound is administered interperitoneally.

21. The method of claim 15 wherein the compound is administered interperitoneally.

22. The method of claim 17 wherein the compound is administered interperitoneally.

* * * * *